US00PP35992P2

(12) United States Plant Patent
van Sambeek

(10) Patent No.: US PP35,992 P2
(45) Date of Patent: Jul. 9, 2024

(54) ***ERYSIMUM* PLANT NAMED 'DOERYINBRIL'**

(50) Latin Name: *Erysimum hybrida*
Varietal Denomination: Doeryinbril

(71) Applicant: DUMMEN GROUP B.V., De Lier (NL)

(72) Inventor: Ellen van Sambeek, Oegstgeest (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/382,506

(22) Filed: Oct. 21, 2023

(51) Int. Cl.
*A01H 5/02* (2018.01)
*A01H 6/20* (2018.01)

(52) U.S. Cl.
USPC ..... Plt./263.1
CPC ..... *A01H 6/20* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Erysimum* plant named 'Doerinbril', characterized by its upright and mounding plant habit; moderately vigorous growth habit; freely branching habit; dense and bushy habit; freely and continuous flowering habit; long flowering period; large deep red to deep purplish red-colored flowers with yellowish orange-colored centers; and good garden performance.

2 Drawing Sheets

Figure 1:
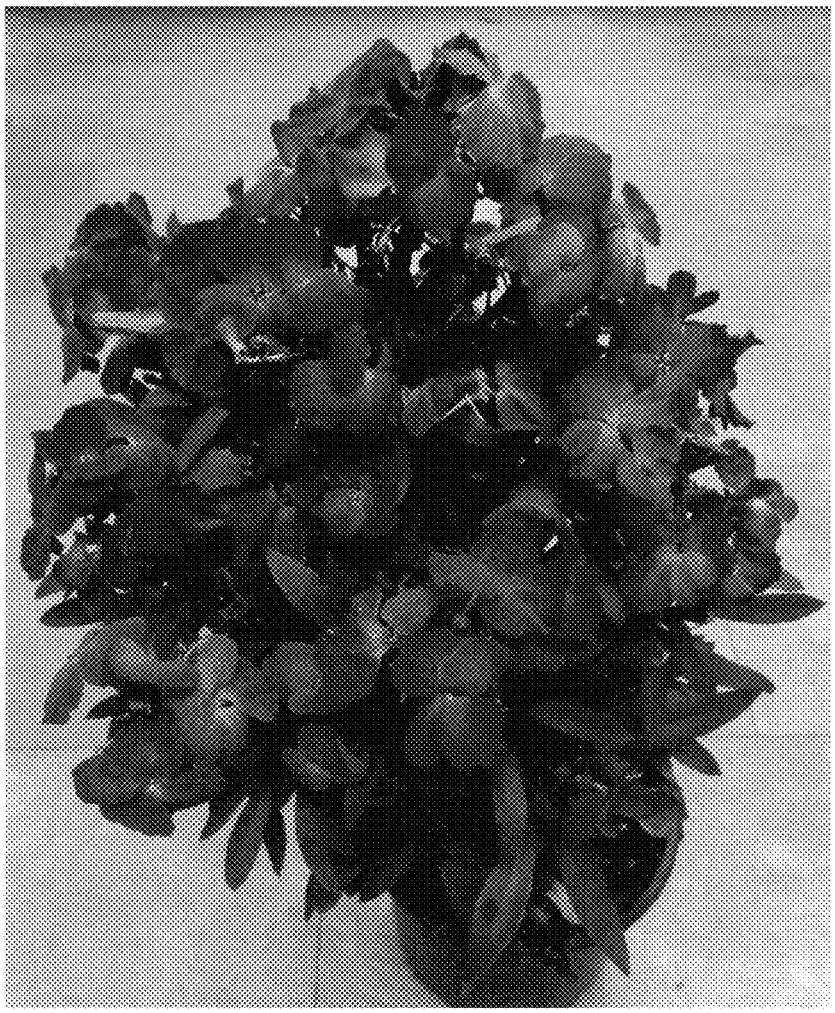

Botanical designation: *Erysimum hybrida.*
Cultivar denomination: 'DOERYINBRIL'.

CROSS-REFERENCED TO CLOSELY-RELATED APPLICATIONS

Title: *Erysimum* Plant Named 'Doeryinyo'
Inventor: Ellen van Sambeek
Applicant: Dummen Group B.V.
Filed: Oct. 21, 2023

STATEMENT REGARDING PRIOR DISCLOSURES BY INVENTOR & APPLICANT/ASSIGNEE

An European Community Plant Breeder's Rights application for the instant plant was filed by the Applicant/Assignee, Dümmen Group B.V. of De Lier, The Netherlands on Jul. 25, 2023, application number 2023/1571. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Erysimum* plant, botanically known as *Erysimum hybrida*, commonly referred to as Wallflower and hereinafter referred to by the name 'Doerinbril'.

The new *Erysimum* plant is a product of a planned breeding program conducted by the Inventor in Aalsmeer, The Netherlands. The objective of the breeding program was to develop new *Erysimum* plants with numerous large and attractive flowers.

The new *Erysimum* plant originated from a cross-pollination in March, 2018 in Aalsmeer, The Netherlands of a proprietary selection of *Erysimum hybrida* identified as code number ER17-000004-003, not patented, as the female, or seed, parent, with a proprietary selection of *Erysimum hybrida* identified as code number ER-0015, not patented, as the male, or pollen, parent. The new *Erysimum* plant was discovered and selected by the Inventor as a single flowering plant within the progeny of the stated cross-pollination in a controlled greenhouse environment in Aalsmeer, The Netherlands in March, 2019.

Asexual reproduction of the new *Erysimum* plant by vegetative terminal cuttings in a controlled greenhouse environment in Aalsmeer, The Netherlands since March, 2019 has shown that the unique features of this new *Erysimum* plant are stable and reproduced true to type in successive generations.

SUMMARY OF THE INVENTION

Plants of the new *Erysimum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Doerinbril'. These characteristics in combination distinguish 'Doerinbril' as a new and distinct *Erysimum* plant:

1. Upright and mounding plant habit.
2. Moderately vigorous growth habit.

3. Freely branching habit; dense and bushy habit.
4. Freely and continuous flowering habit.
5. Long flowering period.
6. Large deep red to deep purplish red-colored flowers with yellowish orange-colored centers.
7. Tolerant to low and high temperatures and good garden performance.

Plants of the new *Erysimum* differ primarily from plants of the female parent selection in flower color as flowers of plants of the new *Erysimum* are deep red to deep purplish red in color with yellowish orange-colored centers whereas flowers of plants of the female parent selection are orange in color.

Plants of the new *Erysimum* differ primarily from plants of the male parent selection in flower color as flowers of plants of the new *Erysimum* are deep red to deep purplish red in color with yellowish orange-colored centers whereas flowers of plants of the male parent selection are red tinged with purple in color.

Plants of the new *Erysimum* can be compared to *Erysimum hybrida* 'Doeryinyo', disclosed in U.S. Plant patent application Ser. No. 18/382,507 filed concurrently. Plants of the new *Erysimum* differ primarily from plants of 'Doeryinyo' in flower color as flowers of plants of the new *Erysimum* are deep red to deep purplish red in color with yellowish orange-colored centers whereas flowers of plants of 'Doeryinyo' are dark red to dark purplish red and reddish purple in color. In addition, plants of the new *Erysimum* are not as vigorous as plants of 'Doeryinyo'.

Plants of the new *Erysimum* can also be compared to *Erysimum hybrida* 'Poem Pastel', not patented. In side-by-side comparisons, plants of the new *Erysimum* differ from plants of 'Poem Pastel' in the following characteristics:

1. Plants of the new *Erysimum* have larger leaves than plants of 'Poem Pastel'.
2. Plants of the new *Erysimum* have larger flowers than plants of 'Poem Pastel'.
3. Flowers of plants of the new *Erysimum* are deep red to deep purplish red in color with yellowish orange-colored centers whereas flowers of plants of 'Poem Pastel' are pastel pink and yellow in color.

BRIEF DESCRIPTION OF THE PHOTOGRAPHS

The accompanying colored photographs illustrate the overall appearance of the new *Erysimum* plant showing the colors as true as it is reasonably possible to obtain in colored reproductions of this type. Colors in the photographs may differ slightly from the color values cited in the detailed botanical description which accurately describe the colors of the new *Erysimum* plant.

The photograph on the first sheet (FIG. 1) is a side perspective view of a typical flowering plant of 'Doerinbril' grown in a container.

Figure 2:
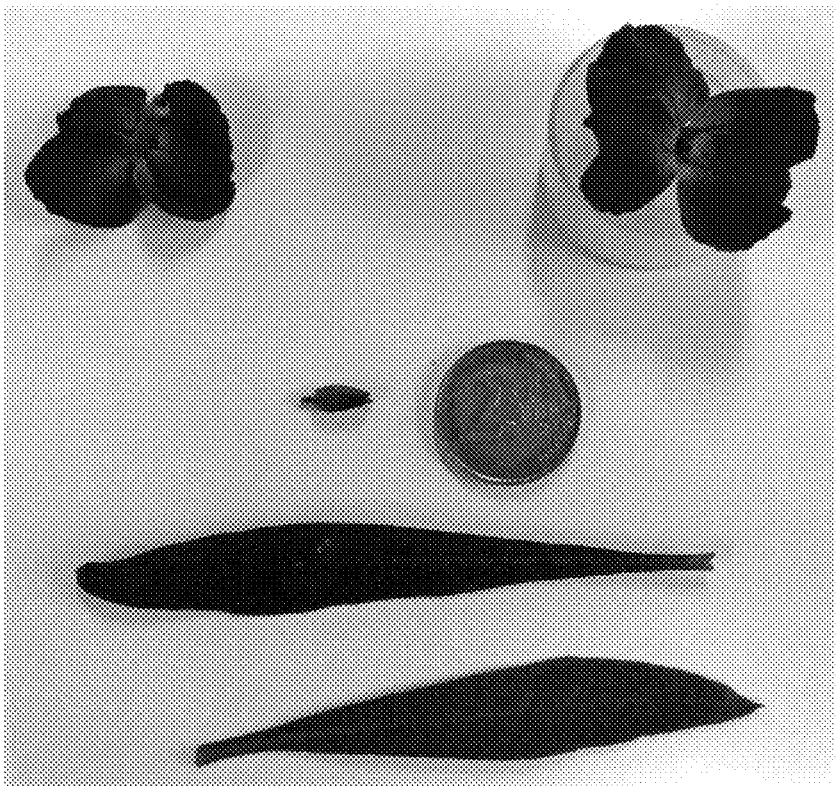

The photograph on the second sheet (FIG. 2) is a close-up view of a typical flower bud and the upper and lower surfaces of typical leaves and flowers.

DETAILED BOTANICAL DESCRIPTION

The aforementioned photographs and following observations and measurements describe plants grown during the early spring in 17-cm containers in a glass-covered greenhouse in Aalsmeer, The Netherlands and under cultural practices typical of commercial *Erysimum* production. During the production of the plants, average daily temperatures were 21 C and average night temperatures were 15 C. Plants were 28 weeks old when the photographs and description were taken. In the following description, color references are made to The Royal Horticultural Society Colour Chart, Second Edition, except where general terms of ordinary dictionary significance are used.

Botanical classification: *Erysimum hybrida* 'Doerinbril'.

Parentage:

*Female, or seed, parent*.—Proprietary selection of *Erysimum hybrida* identified as code number ER17-000004-003, not patented.

*Male, or pollen, parent*.—Proprietary selection of *Erysimum hybrida* identified as code number ER-0015, not patented.

Propagation:

*Type*.—Terminal vegetative cuttings.

*Time to initiate roots, summer*.—About twelve days at temperatures about 26 C.

*Time to initiate roots, winter*.—About 16 days at temperatures about 23 C.

*Time to produce a rooted young plant, summer*.—About 16 days at temperatures about 23 C.

*Time to produce a rooted young plant, winter*.—About 20 days at temperatures about 18 C.

*Root description*.—Medium in thickness, fibrous; typically white in color, actual color of the roots is dependent on substrate composition, water quality, fertilizer type and formulation, substrate temperature and physiological age of roots.

*Rooting habit*.—Moderately freely branching; medium density.

Plant description:

*Plant form and growth habit*.—Perennial garden or container plant; upright and mounding plant habit; freely branching habit with about 29 lateral branches developing per plant; dense and bushy appearance; moderately vigorous growth habit.

*Plant height*.—About 40 cm.

*Plant diameter* (*area of spread*).—About 35 cm.

*Lateral branches*.—Length: About 24 cm. Diameter: About 5 mm. Internode length: About 5 mm. Strength: Strong. Aspect: About 20 to 40 degrees from vertical. Texture and luster: Smooth, glabrous; glossy. Color, developing: Close to 143A. Color, developed: Close to 144A.

Leaf description:

*Arrangement*.—Alternate; simple; sessile. Length: About 10 cm. Width: About 1.5 cm. Shape: Oblanceolate. Apex: Acute. Base: Cuneate. Margin: Entire.

*Texture and luster, upper surface*.—Pubescent; glossy.

*Texture and luster, lower surface*.—Pubescent; semi-glossy.

*Venation pattern*.—Single midvein discernible.

*Color*.—Developing leaves, upper surface: Close to 137A. Developing leaves, lower surface: Close to 137C. Fully developed leaves, upper surface: Close to 147A; venation, close to 144A. Fully developed leaves, lower surface: Close to 146A; venation, close to 146A.

Flower description:

*Flower type and habit*.—Large rounded cruciform flowers arranged in dense racemes; flowers face mostly upright to outwardly; freely flowering habit, about five flowers per inflorescence and about 328 flowers developing per plant during the flowering season.

*Natural flowering season*.—Plants of the new *Erysimum* begin flowering about 20 weeks after planting; relatively long flowering period, plants flower continuously from spring until autumn in The Netherlands; flowers not persistent.

*Fragrance*.—Moderately fragrant; sweet, pleasant.

*Inflorescence height*.—About 4.5 cm.

*Inflorescence diameter*.—About 6 cm.

*Flower diameter*.—About 3.8 cm.

*Flower depth* (*height*).—About 1.5 cm.

*Flower buds*.—Length: About 1.4 cm. Diameter: About 6 mm. Shape: Elliptic. Texture and luster: Smooth, glabrous; matte. Color: Close to 187A.

*Petals*.—Quantity and arrangement: Four petals arranged in a single whorl. Length: About 1.8 cm. Width: About 2.2 cm. Shape: Obovate. Apex: Obtuse with truncate tendencies. Base: Cuneate. Margin: Entire; sinuate. Texture and luster, upper surface: Smooth, glabrous; semi-glossy. Texture and luster, lower surface: Smooth, glabrous; matte. Color: When opening, upper and lower surfaces: Close to 46A. Fully opened, upper surface: During development, flowers transition through the following colors, close to 46A, 45A and 53A; towards the base, close to 21A and 28A; venation, close to 53A and 61A. Fully opened, lower surface: During development, flowers transition through the following colors, close to 46A, 45A and 53A; venation, close to 53A and 61A.

*Sepals*.—Quantity and arrangement: Four sepals arranged in a single whorl; calyx, tubular. Calyx length: About 1.3 cm. Calyx diameter: About 6 mm. Length: About 1.3 cm. Width: About 4 mm. Shape: Subulate. Apex: Acuminate. Base: Cuneate. Margin: Entire. Texture and luster, upper and lower surfaces: Smooth, glabrous; glossy. Color, upper surface: Close to 146A. Color, lower surface: Close to 144B.

*Pedicels*.—Length: About 5 mm. Width: About 1 mm. Strength: Flexible. Aspect: About 45 to 60 degrees from vertical. Texture and luster: Smooth, glabrous; glossy. Color: Close to 146A.

*Reproductive organs*.—Stamens: Quantity per flower: Six. Filament length: About 1 cm. Filament color: Close to 145D. Anther shape: Deltoid. Anther size: About 1 mm by 4 mm. Anther color: Close to 153A. Pollen amount: Abundant. Pollen color: Close to 158A. Pistils: Quantity per flower: One. Pistil length: About 1.1 cm. Style length: About 2 mm. Style color: Close to 144A. Stigma diameter: About 2 mm. Stigma shape: Rounded, capitate. Stigma color: Close to 145A. Ovary color: Close to 155D.

*Seeds/fruits*.—To date, seed and fruit development has not been observed on plants of the new *Erysimum*.

Pathogen & pest resistance: To date, plants of the new *Erysimum* have not been noted to be resistant to pathogens or pests common to *Erysimum* plants.

Garden performance: Plants of the new *Erysimum* have been observed to have good garden performance and to tolerate temperatures ranging from about −20 C to about 35 C and are suitable for U.S.D.A. Hardiness Zone 6.

It is claimed:

1. A new and distinct *Erysimum* plant named 'Doeryinbril' as illustrated and described.

* * * * *